US00PP08535P

United States Patent [19]

Musacchi et al.

[11] Patent Number: Plant 8,535

[45] Date of Patent: Jan. 11, 1994

[54] STRAWBERRY PLANT NAMED ONEBOR

[75] Inventors: Dario Musacchi; Michelangelo Leis, both of Ferrara, Italy

[73] Assignee: C.I.V. Consorzio Italiano Vivaisti, Italy

[21] Appl. No.: 841,041

[22] Filed: Feb. 25, 1992

[51] Int. Cl.[5] ..... A01H 5/00

[52] U.S. Cl. ..... Plt./48

[58] Field of Search ..... Plt. 48, 49

*Primary Examiner*—James R. Feyrer

*Attorney, Agent, or Firm*—Christie, Parker & Hale

[57] ABSTRACT

A new variety of strawberry named 'Onebor' suitable for culture under glass and for water culture and for growing in a cool-temperate climate to produce fruit that keeps well and that is resistant to handling and transport.

2 Drawing Sheets

BACKGROUND OF THE INVENTION

The new variety of strawberry was created in a breeding program conducted in Ferrara, Italy and was originated by crossing the variety known as 'Gorella', as female parent, with the variety known as 'Selezione No. 15' as male parent. 'Selezione' is a proprietary unreleased variety maintained for breeding purposes. The new variety was grown as a seedling and asexually propagated by stolen in Ferrara, Italy. Clones of the new variety were further asexually propagated and extensively tested. This propagation and testing demonstrated that the combination of traits disclosed herein that characterize the new variety are fixed and retained true to type through successive generations of asexual reproduction.

SUMMARY OF THE INVENTION

The present invention relates to a new and distinct strawberry variety. The varietal denomination of the new variety is 'Onebor'. Among the distinguishing characteristics of the new variety are the combination of traits which include high fruit productivity, production of comparatively large sized and very regular conically-shaped fruit with few imperfectly formed fruit. The new variety is particularly suitable for culture under glass and for water culture, i.e., hydroponics.

As to the classification of the new strawberry variety, 'Onebor' is considered a "long-day variety" by which is meant a variety in which the differentiation to flower (that is the passage from the vegetative phase to reproductive phase) takes place only if the length of the light period exceeds a certain value (normally about 12–15 hours a day). 'Onebor' is not an everbearing remontant variety.

The flowering starts around April 22 (in Ferrara, Italy) (five days later than 'Gorella') and lasts up to May 1st (ten days later than 'Gorella'). In open field cultivation in the zone of Ferrara (Northern Italy), where the field trials concerning the variety 'Onebor' were carried out, the plants of the variety 'Onebor' bear fruit between mid May and mid June. There is no prolonged production such as in the case of varieties normally grown in the central and southern areas of California. 'Onebor' is a medium ripening variety and its average harvesting period is between May 25 and June 15 (in the zone of Ferrara). Similar periods of production may be obtained in northern California, Oregon, Washington and generally in the North East, which are possible growing areas for the variety 'Onebor'.

COMPARISON TO THE CLOSEST VARIETY

The new variety is most similar to the variety 'Gorella' but is distinguished therefrom by the following characteristics:

1. The new variety has greater sprouting than 'Gorella'.

2. 'Onebor' is less sensitive to downy mildew (oidium) and leaf spot than is the variety 'Gorella'.

3. The new variety flowers much more extensively over a longer time and the flowers are richer in pollen. Fruit of the new variety are conically shaped and more regular than 'Gorella' and have brighter color, i.e., near 44A, with better flesh firmness. The new variety is more fruit-productive than 'Gorella'.

4. The new variety produces an average of about 3.2 stems per crown; whereas 'Gorella' produces about 2.5 stems per crown.

In addition to the foregoing, 'Onebor' produces a greater number of flowers than the variety 'Gorella' and the flowers produce pollen in a greater quantity than the flowers of the variety 'Gorella'. This ensures a better pollination also in primary flowers. The fruit of 'Onebor' are, on the average, larger than the fruit of 'Gorella'. The average weight of the fruit of 'Onebor' (determined in field trials carried out in the zone of Ferrara in 1991), was of 18.40 g/fruit, while in the case of 'Gorella' the average weight was of 12.50 g/fruit. The difference is mainly due to the larger size of the secondary and tertiary fruit. In 'Onebor', secondary and tertiary fruit maintain an average weight of 18 g, while in 'Gorella' the average weight of secondary and tertiary fruit is 10 g. The shape of the fruit of 'Onebor' is more regular and less sensitive to deformation than 'Gorella'. This difference is also due to the better pollination. The color of the fruit of 'Onebor' with respect to the variety 'Gorella' is practically the same but more homogeneous, that is, the same on the whole surface of the fruit, and brighter.

BRIEF DESCRIPTION OF THE ILLUSTRATIONS

The accompanying photographs show typical specimens of the new variety in color as is nearly true as it is possible to make in color illustrations of this character.

One illustration shows typical fruit against the background of the plants foliage.

Another illustration shows cross sectional and longitudinal views of mature fruit illustrating surface and flesh coloration and conspicuous core and core cavity.

Still another illustration shows typical flower and reproduction organs, including petals and fruit bases.

DESCRIPTION OF THE NEW VARIETY

The following is a detailed description of the new variety with color terminology in accordance with the Royal Horticultural Society Colour Chart (RHSCC). The terminology used in the color description herein refers to the plate numbers in the aforementioned color chart. Color designations, color descriptions, and phenotypical descriptions may deviate from the stated values and description depending upon varying climatic, environmental, seasonal and cultural conditions.

The information provided herein is based upon observations taken in the region of Ferrara, Italy, during the period March to June 1991 of plants grown outdoor.

Propagation

The new variety propagates easily by stolens and is quick rooting. The plants root very well after transplanting. Although propagation by stolens is presently preferred, other known methods of propagations for strawberry may be employed.

Plant

Plants of the new variety are quite compact; growing to approximately 16 to 22 cm. in height. The plant has very good fruit production and only requires planting periods appropriate to particular environments. However, very early transplanting causes excessive flower differentiation and plant stress. In regions having growing conditions similar to that where these observations were made, the recommended planting period is the first ten days in August. Maximum production in this region outdoors occurs between May 25, and June 15.

Growth habit of the new variety is erect achieving a medium height diameter and of average vigor. The new variety appears to be suitable for growing in areas favored by cool-temperate climates with maximum temperatures that are not excessive or extended.

It has been observed that the plant has good resistance to principal root illnesses and to downy mildew. It is also resistant to frost.

The new variety has a short strong peduncle from which a primary pedicel, substantially aligned with the peduncle, and one or more than one secondary pedicels branch off. The secondary pedicels form a substantially obtuse angle with the peduncle and are shorter and thinner than the primary pedicel. One or more than one tertiary pedicels branch off the secondary pedicel forming a substantially obtuse angle with the secondary pedicel. The tertiary pedicels are shorter and thinner than the secondary pedicels. In comparison with the secondary and tertiary pedicels of the variety 'Gorella', the secondary and tertiary pedicels of the variety 'Onebor' are longer so that all the fruit, primary, secondary and tertiary, are located outside the canopy.

Foliage

Leaves are of medium size, regularly shaped and of generally equal length and breadth. The leaves tend to be of medium thickness with weak hairiness on the upper side and medium hairiness on the reverse side. The upper side tends to be spoon-shaped with medium blistering and highly prominent venation. The top surface of the leaves is near 139A with no secondary coloration, and is of medium glossiness. Leaves are compound three-leaflets leaves with an upward growth habit relative to the petiole, and upwardly curved margins, obtuse angles at the V-shaped base, incisions intermediate between serrate and crenate, and with occasional occurrence of secondary incisions. The terminal leaflet is five to eight cm. long and five to eight cm. wide.

The petioles are medium sized, 12 to 17 cm. in length, with medium hairiness on the upper third section and an outward arrangement of hairs. The stipules are of medium length with a slight anthocyanic coloration. The stolens are average in number and also with anthocyanic coloration, weak hairiness and upward arrangement of the hairs.

The inflorescence emerges from the foliage with a thick pedicel of medium hairiness and with slightly upwardly oblique hairs.

Flowers

The flowering time for the new variety is average but the flowering is rich and extended, producing large, pollen-rich bisexual flowers. The number of petals is five to eight on the primary flowers and five to six on secondary flowers and are generally as large as they are wide with a very obtuse angle at the base and very weak undulation of the margins. The petals are imbricated and overlap. The calyx is smaller than the corolla and of medium hairiness on the lower part. The sepals have an extended shape and are medium green in color. The flowers appear above the foliage and on strong stems. There is significant branching with the first branching beginning close to the base.

Fruit

Fruit of the new variety are comparatively large and predominantly conically-shaped, although some primary fruit is flattened. The color of the fruit surface is red, near 44A, homogeneous and very bright. The achenes are found below the surface.

The flesh of the fruit appears red, near 40B, and is nonuniformly spread, of high consistency, medium sweetness and acidity and moderate aroma. The ripening time in the region in which the observations are made is about five days. Separation from the calyx is of medium difficulty. The fruit keeps well and is resistant to handling and transport.

A core cavity is formed in the first or second fruit which are of large size. The other fruit do not show any core cavity. The achenes for the most part are below the surface. The fruit or parts of the fruit more exposed to cold may show the achenes protruding from the surface.

We claim:

1. A new and distinct strawberry variety substantially as shown and described.

* * * * *

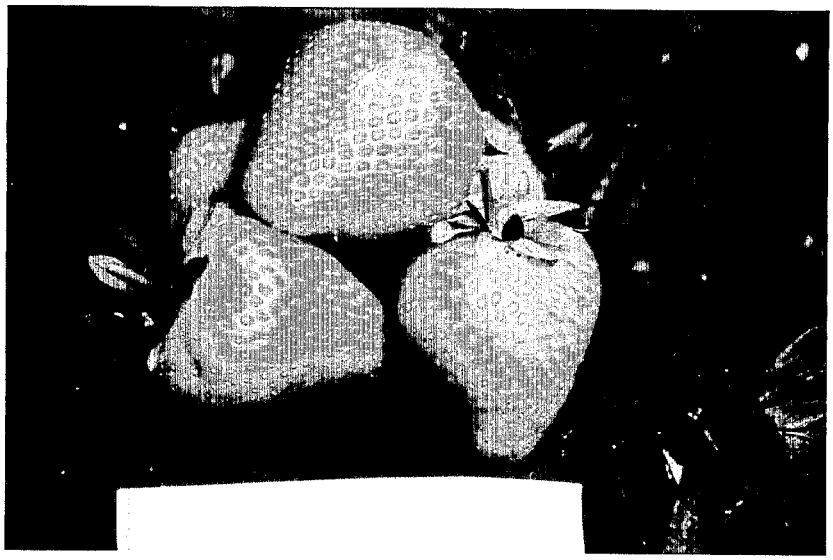
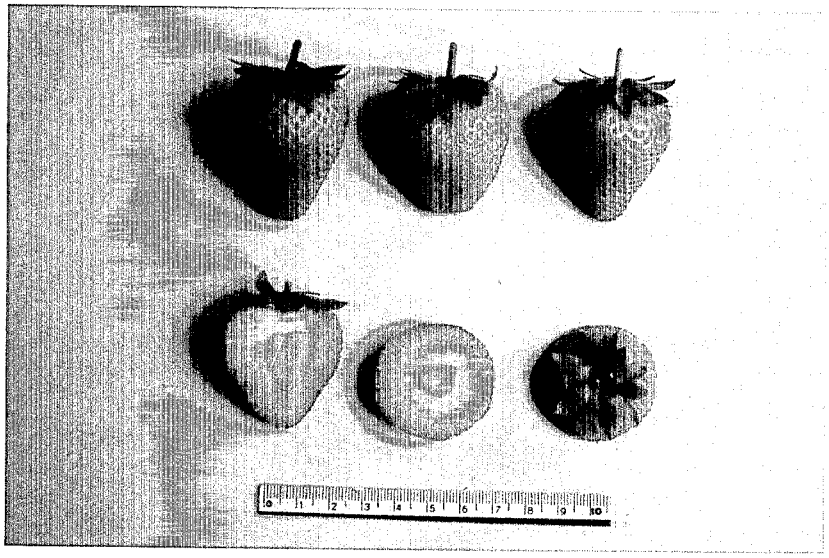

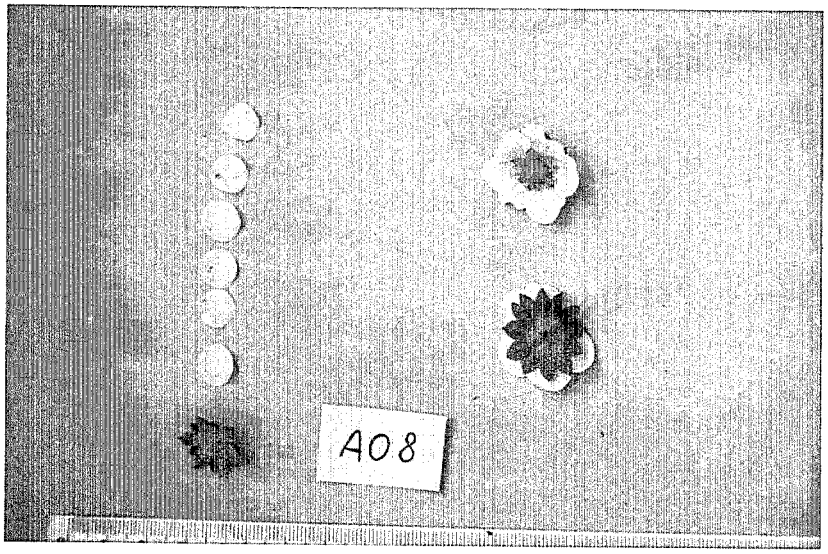
A08